United States Patent
Takahashi

(10) Patent No.: US 9,723,975 B2
(45) Date of Patent: Aug. 8, 2017

(54) CAPSULE ENDOSCOPE SYSTEM DETERMINING OPERATION OF DISPLAY AND POSITION DETECTION

(71) Applicant: OLYMPUS CORPORATION, Tokyo (JP)

(72) Inventor: Kazuhiko Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/963,857

(22) Filed: Dec. 9, 2015

(65) Prior Publication Data
US 2016/0089009 A1 Mar. 31, 2016

Related U.S. Application Data

(63) Continuation of application No. PCT/JP2014/070947, filed on Aug. 7, 2014.

(30) Foreign Application Priority Data

Aug. 28, 2013 (JP) .................. 2013-177231

(51) Int. Cl.
*A61B 1/00* (2006.01)
*A61B 1/04* (2006.01)
(Continued)

(52) U.S. Cl.
CPC .......... *A61B 1/041* (2013.01); *A61B 1/00016* (2013.01); *A61B 1/00045* (2013.01);
(Continued)

(58) Field of Classification Search
CPC .......... A61B 1/04; A61B 1/041; A61B 1/045; A61B 1/05; A61B 1/06; A61B 1/00009;
(Continued)

(56) References Cited

U.S. PATENT DOCUMENTS 8,194,096 B2 6/2012 Hirakawa et al.
8,214,017 B2 7/2012 Sato et al.
(Continued)

FOREIGN PATENT DOCUMENTS

CN 102843950 A 12/2012
JP 2009-213613 A 9/2009
(Continued)

OTHER PUBLICATIONS

International Search Report dated Nov. 11, 2014 issued in PCT/JP2014/070947.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A capsule endoscope system includes: a capsule endoscope; a receiving unit that receives an image signal of an object transmitted wirelessly from the capsule endoscope; an image display unit that displays an image based on the image signal received by the receiving unit; a position detection unit that detects a position of the capsule endoscope; and a control unit having a first determination unit that determines whether normal display of the image based on the image signal is possible and having a second determination unit that determines whether normal position detection for the capsule endoscope is possible by the position detection unit. The control unit causes the image display unit to start display of the image based on the image signal when the normal display of the image based on the image signal is possible and the normal position detection for the capsule endoscope is possible.

7 Claims, 8 Drawing Sheets

(51) Int. Cl.
*A61B 1/06* (2006.01)
*A61B 1/045* (2006.01)
*A61B 5/06* (2006.01)

(52) U.S. Cl.
CPC ............ *A61B 1/045* (2013.01); *A61B 1/0002* (2013.01); *A61B 1/00006* (2013.01); *A61B 1/00009* (2013.01); *A61B 1/00025* (2013.01); *A61B 1/00055* (2013.01); *A61B 5/065* (2013.01)

(58) Field of Classification Search
CPC ............ A61B 1/00043; A61B 1/00055; A61B 1/00057; A61B 1/00062; A61B 1/00016; A61B 5/065
USPC ....... 600/103, 109, 117, 118, 160, 302, 309, 600/310; 348/65
See application file for complete search history.

(56) References Cited

U.S. PATENT DOCUMENTS

| | | | | |
|---|---|---|---|---|
| 2008/0267466 | A1* | 10/2008 | Fujita | A61B 1/00004 382/128 |
| 2009/0046821 | A1* | 2/2009 | Shigemori | A61B 1/00016 375/371 |
| 2009/0177036 | A1* | 7/2009 | Shimizu | A61B 1/041 600/117 |
| 2009/0312601 | A1 | 12/2009 | Shigemori | |
| 2010/0022833 | A1* | 1/2010 | Nagase | A61B 1/041 600/118 |
| 2011/0213205 | A1 | 9/2011 | Uchiyama et al. | |
| 2012/0203068 | A1 | 8/2012 | Sato et al. | |
| 2012/0274743 | A1 | 11/2012 | Takasugi et al. | |
| 2013/0117696 | A1* | 5/2013 | Robertson | G06F 19/3418 715/763 |
| 2014/0163357 | A1 | 6/2014 | Higaki et al. | |

FOREIGN PATENT DOCUMENTS

WO    WO 2007/119784 A1    10/2007
WO    WO 2013/018464 A1    2/2013

OTHER PUBLICATIONS

Japanese Office Action dated Aug. 11, 2015 issued in JP 2015-507837.
Japanese Office Action dated Jun. 3, 2015 issued in JP 2015-507837.
Chinese Office Action dated Nov. 2, 2016 in related Chinese Patent Application No. 201480030105.X.
Extended Supplementary European Search Report dated Feb. 8, 2017 in European Patent Application No. 14 84 0350.4.

* cited by examiner

CAPSULE ENDOSCOPE SYSTEM DETERMINING OPERATION OF DISPLAY AND POSITION DETECTION

CROSS-REFERENCE TO RELATED APPLICATIONS

This application is a continuation of PCT international application Ser. No. PCT/JP2014/070947 filed on Aug. 7, 2014 which designates the United States, incorporated herein by reference, and which claims the benefit of priority from Japanese Patent Application No. 2013-177231, filed on Aug. 28, 2013, incorporated herein by reference.

BACKGROUND

1. Technical Field

The disclosure relates to a capsule endoscope system for introducing a capsule endoscope into a subject to observe the inside of the subject.

2. Related Art

In recent years, a capsule endoscope that is formed in a size insertable into the digestive tract of a subject, for example, a patient has been under development in the field of endoscope. The capsule endoscope is a device that is provided with an imaging function and a wireless communication function inside a capsule-shaped casing. The capsule endoscope is swallowed through the mouth of a subject, then sequentially images the inside of the digestive tract of the subject while moving inside the digestive tract by, for example, peristaltic movement to acquire an image signal, and transmits the acquired image signal to the outside of the subject. The image signal is received through a plurality of antennas disposed on the body surface of the subject, subjected to predetermined signal processing, and then output to an image display device. The image display device displays an image based on the image signal as a still image or a moving image. A doctor observes the image of the inside of the digestive tract (hereinafter, also referred to as an in-vivo image) displayed in this manner to diagnose a state of the digestive tract of the subject.

Such a capsule endoscope system has a function of detecting the position of the capsule endoscope inserted into the subject. For example, there is known a technique that estimates the position of a capsule endoscope by providing a coil that generates an alternating magnetic field in the capsule endoscope and detecting the alternating magnetic field by a plurality of sense coils placed outside a subject (refer to JP 2009-213613 A, for example). Alternatively, the position of the capsule endoscope may be estimated on the basis of the strength of an image signal received by each of a plurality of antennas.

Typically, a capsule endoscope system has an examination management function of managing an examination. Image signals and positional information of a capsule endoscope are generated and then sequentially stored in association with an examination file issued by the examination management function.

SUMMARY

In some embodiments, a capsule endoscope system includes: a capsule endoscope having an imaging unit configured to image an object to generate an image signal and having a wireless communication unit configured to wirelessly transmit the image signal generated by the imaging unit; a receiving unit configured to receive the image signal transmitted from the capsule endoscope; an image display unit configured to display an image based on the image signal received by the receiving unit; a position detection unit configured to detect a position of the capsule endoscope; and a control unit having a first determination unit configured to determine whether normal display of the image based on the image signal is possible and having a second determination unit configured to determine whether normal position detection for the capsule endoscope is possible by the position detection unit. The control unit is configured to cause the image display unit to start display of the image based on the image signal when the first determination unit determines that the normal display of the image based on the image signal is possible and the second determination unit determines that the normal position detection for the capsule endoscope is possible.

The above and other features, advantages and technical and industrial significance of this invention will be better understood by reading the following detailed description of presently preferred embodiments of the invention, when considered in connection with the accompanying drawings.

DETAILED DESCRIPTION

A capsule endoscope system according to some embodiments of the present invention will be described below with reference to the drawings. Although, in the following, a capsule endoscope that is configured to be inserted into a subject through the mouth and to image the inside of the subject (the inside of the digestive tract) while being guided by a magnetic field applied from the outside will be described as an example, the present invention is not limited by the embodiments. That is, the present invention may use various capsule endoscopes such as a capsule endoscope that images the inside of the digestive tract while moving from the esophagus through the anus of a subject by peristaltic movement or a capsule endoscope that is inserted from the anus together with an isotonic solution. In the following description, each of the drawings merely illustrates shape, size, and positional relationship schematically enough to enable understanding of the contents of the present invention. Thus, the present invention is not limited only to the shape, size, and positional relationship illustrated in each of the drawings. The same reference signs are used to designate the same elements throughout the drawings.

Embodiments

Figure 1:
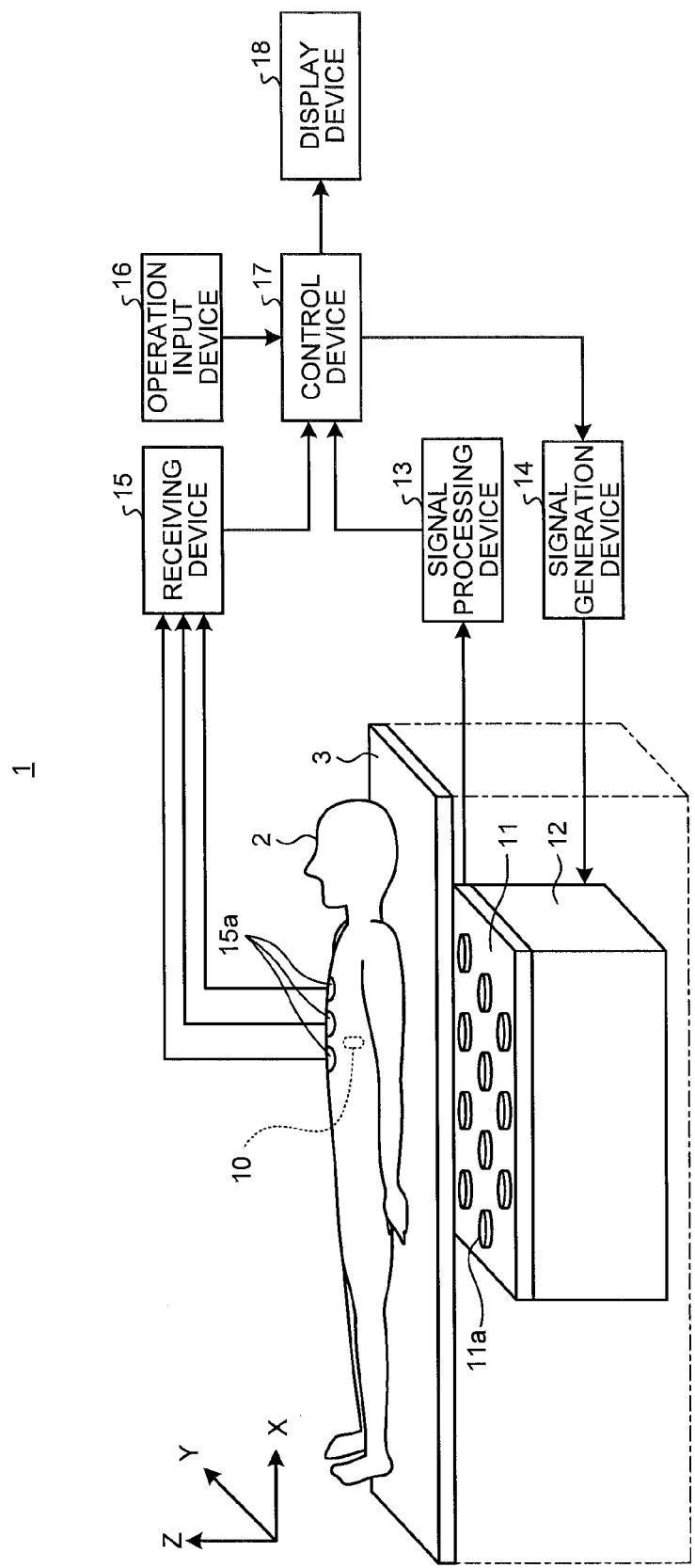
FIG. 1 is a diagram illustrating an example of the configuration of a capsule endoscope system according to an embodiment of the present invention.

FIG. 1 is a diagram illustrating an example of the configuration of the capsule endoscope system according to the embodiment of the present invention. As illustrated in FIG. 1, the capsule endoscope system 1 according to the embodiment is provided with a capsule endoscope 10 which is inserted into the digestive tract of a subject 2 and wirelessly transmits an image signal acquired by imaging the inside of the subject 2, a position detection device 11 and a magnetic field generation device 12 which are placed under a bed 3 on which the subject 2 is placed, a signal processing device 13 which processes a signal output from the position detection device 11, a signal generation device 14 which generates a signal for operating the magnetic field generation device 12, a receiving device 15 which receives an image signal transmitted from the capsule endoscope 10, an operation input device 16 for guiding and operating the capsule endoscope 10, a control device 17 which performs processing for displaying an image inside the subject 2 (hereinafter, referred to as an in-vivo image) in accordance with an image signal received by the receiving device 15, and a display device 18 which displays an in-vivo image or other information.

The bed 3 is placed with an upper face (a placement face on which the subject 2 is to be placed) parallel to a horizontal plane (a plane perpendicular to the gravity direction). In the following description, a longitudinal direction of the bed 3 is defined as an X direction, a transverse direction of the bed 3 is defined as a Y direction, and a vertical direction (gravity direction) is defined as a Z direction.

Figure 2:
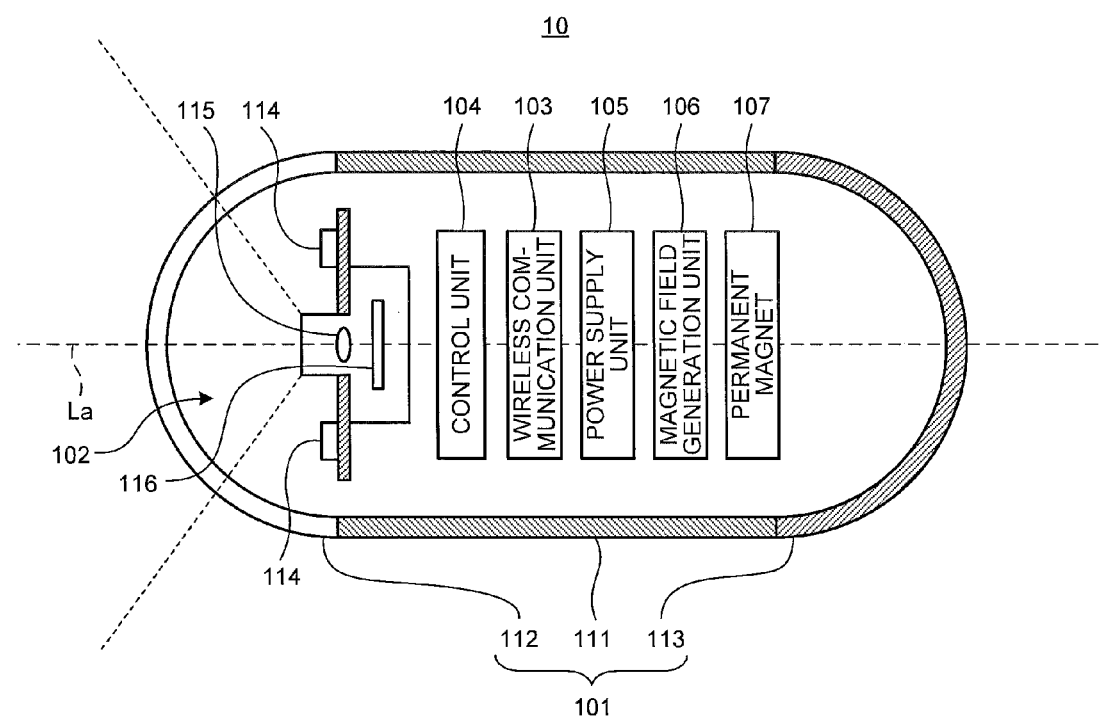
FIG. 2 is a schematic diagram illustrating an example of the internal structure of a capsule endoscope illustrated in FIG. 1.

FIG. 2 is a schematic diagram illustrating an example of the internal structure of the capsule endoscope 10. As illustrated in FIG. 2, the capsule endoscope 10 is provided with a capsule-shaped casing 101 which is an outer sheath formed in a size easily insertable into the internal organs of the subject 2, an imaging unit 102 which images an object to generate an image signal, a wireless communication unit 103 which wirelessly transmits an image signal generated by the imaging unit 102 to the outside, a control unit 104 which controls each constituent unit of the capsule endoscope 10, a power supply unit 105 which supplies electric power to each element of the capsule endoscope 10, a magnetic field generation unit 106 which generates an alternating magnetic field for detecting the position of the capsule endoscope 10, and a permanent magnet 107 for enabling magnetic induction by the magnetic field generation device 12.

The capsule-shaped casing 101 is an outer casing which is formed in a size insertable into the internal organs of the subject 2 and formed by blocking both opening ends of a tubular casing 111 with dome-shaped casings 112 and 113. The dome-shaped casing 112 is a dome-shaped optical member that is transparent to light having a predetermined wavelength band such as visible light. The tubular casing 111 and the dome-shaped casing 113 are colored casings that are substantially opaque to visible light. The capsule-shaped casing 101 which includes the tubular casing 111 and the dome-shaped casings 112 and 113 liquid-tightly encloses therein the imaging unit 102, the wireless communication unit 103, the control unit 104, the power supply unit 105, the magnetic field generation unit 106, and the permanent magnet 107 as illustrated in FIG. 2.

The imaging unit 102 includes an illumination unit 114 such as an LED, an optical system 115 such as a condenser lens, and an imaging element 116 such as a CMOS image sensor and a CCD. The illumination unit 114 emits illumination light such as white light to an imaging view field of the imaging element 116 to illuminate an object within the imaging view field through the dome-shaped casing 112. The optical system 115 concentrates reflected light from the imaging view field on an imaging surface of the imaging element 116 to form an object image. The imaging element 116 receives the reflected light from the imaging view field concentrated on the imaging surface and photoelectric-converts the received optical signal to generate an image signal that indicates the object image in the imaging view field, that is, an in-vivo image of the subject 2.

In the embodiment, only one imaging unit 102 is provided in the capsule endoscope 10. Alternatively, an additional imaging unit 102 may be provided in the dome-shaped casing 113 to enable imaging of the front side and the rear side of a long axis La. In this case, the dome-shaped casing 113 is also formed of an optical member that is transparent to light having a predetermined wavelength band such as visible light. Further, in this case, the two imaging units 102 are disposed in such a manner that optical axes of the respective imaging units 102 are substantially parallel to or substantially aligned with the long axis La which is a central axis in the longitudinal direction of the capsule-shaped casing 101 and imaging view fields of the respective imaging units face opposite directions.

The wireless communication unit 103 sequentially wirelessly transmits image signals generated by the imaging unit 102 to the outside through an antenna. More specifically, the wireless communication unit 103 acquires an image signal generated by the imaging unit 102 from the control unit 104 and applies signal processing such as modulation to the image signal to generate a wireless signal. The wireless communication unit 103 transmits the wireless signal to the receiving device 15 which is provided outside the subject 2. In this case, the wireless communication unit 103 transmits related information such as a capsule unique ID for identifying a transmission source capsule endoscope 10 together with the image signal. The related information is transmitted using a period in which the image signal itself is not transmitted. Thereafter, the image signal having a vertical synchronization signal that indicates the start of one frame and is embedded on the head of the image signal is transmitted.

The control unit 104 controls the operation of the imaging unit 102 and the operation of the wireless communication unit 103 and controls input and output of signals between the constituent units of the imaging unit 102 and the wireless communication unit 103. Specifically, every time when the imaging element 116 generates an image signal, the control unit 104 acquires the image signal and applies predetermined signal processing to the image signal, and controls the wireless communication unit 103 so as to sequentially wirelessly transmit image signals to the outside along a time series.

The power supply unit 105 is a power storage unit such as a button battery and a capacitor and includes a switch unit such as a magnetic switch and an optical switch. When the power supply unit 105 includes a switch unit composed of a magnetic switch, on and off states of the power are switched by a magnetic field applied from the outside. In an on state, the power supply unit 105 appropriately supplies electric power of the power storage unit to the constituent units of the capsule endoscope 10 (the imaging unit 102, the wireless communication unit 103, the control unit 104, and the magnetic field generation unit 106). In an off state, the power supply unit 105 stops power supply to the constituent units of the capsule endoscope 10.

The magnetic field generation unit 106 constitutes a part of a resonance circuit. The magnetic field generation unit 106 includes a transmission coil which generates a magnetic field by current flowing thereto and a capacitor which forms the resonance circuit together with the transmission coil. The magnetic field generation unit 106 generates an alternating magnetic field having a predetermined frequency upon receiving power supply from the power supply unit 105.

The permanent magnet 107 is disposed in a fixed manner inside the capsule-shaped casing 101 with a magnetization direction inclined with respect to the long axis La. In the embodiment, the permanent magnet 107 is disposed with the magnetization direction perpendicular to the long axis La. The permanent magnet 107 operates following a magnetic field applied from the outside. As a result, magnetic induction of the capsule endoscope 10 by the magnetic field generation device 12 (described below) is achieved.

Referring again to FIG. 1, the position detection device 11 is provided with a plurality of sense coils 11*a* each of which is disposed on a flat panel, and receives an alternating magnetic field generated from the magnetic field generation unit 106 of the capsule endoscope 10 and outputs a detection signal. Each of the sense coils 11*a* includes, for example, a coil spring-shaped tubular coil. The position detection device 11 is placed near the subject 2 during examination. In the embodiment, the position detection device 11 is placed under the bed 3.

The signal processing device 13 captures a detection signal output from each of the sense coils 11*a* of the position detection device 11, then shapes a waveform of the captured detection signal by filter processing, then applies amplification and A/D conversion processing to the detection signal, and then outputs the detection signal as a position detection signal of the capsule endoscope 10 to the control device 17. In the embodiment, the position detection device 11 and the signal processing device 13 constitute a position detection unit for detecting the position of the capsule endoscope 10.

The magnetic field generation device 12 generates a magnetic field for controlling at least either the position or the posture of the capsule endoscope 10 inserted into the subject 2. Specifically, the magnetic field generation device 12 is provided with a plurality of electromagnets and traps the permanent magnet 107 of the capsule endoscope 10 by a composite magnetic field formed from magnetic fields generated from the respective electromagnets in accordance with a signal generated by the signal generation device 14. At this point, the capsule endoscope 10 can be guided to a position and a posture desired by a used by adjusting the magnetic fields generated from the respective electromagnets to change the composite magnetic field.

The signal generation device 14 generates a drive signal for driving each of the electromagnets provided in the magnetic field generation device 12 under the control of the control device 17 (a guidance magnetic field controller 152 describe below).

A guidance method applicable to the capsule endoscope system 1 is not limited to the above configuration that includes the magnetic field generation device 12 and the signal generation device 14, and various known methods may be applied. For example, instead of the magnetic field generation device 12, a permanent magnet (hereinafter, referred to as an external permanent magnet) and a driving unit for moving and rotating the external permanent magnet may be provided. In this case, the position and the posture of the capsule endoscope 10 can be controlled by moving and rotating the external permanent magnet while trapping the permanent magnet 107 of the capsule endoscope 10 by a magnetic field generated by the external permanent magnet.

The receiving device 15 is provided with a plurality of antennas 15*a* which receive a wireless signal transmitted from the capsule endoscope 10 inserted into the subject 2. These antennas 15*a* are housed in a pad and stuck to a predetermined position on the body surface of the subject 2. Alternatively, the subject 2 may wear a jacket to which the plurality of antennas 15*a* are attached (antenna jacket). The receiving device 15 sequentially captures wireless signals from the capsule endoscope 10 received by the respective antennas 15*a* and performs predetermined signal processing such as demodulation processing on a signal captured from an antenna that has the highest received electric field strength to thereby acquire a digital image signal (image data) regarding the inside of the subject 2 and output the acquired digital image signal to the control device 17.

The operation input device 16 is an input device that is used by a user, for example, a doctor to perform various input operations. The operation input device 16 includes, for example, a keyboard and a mouse, a touch penal, a joystick, and an operator console provided with various buttons and various switches. The operation input device 16 outputs a signal to the control device 17 in accordance with an operation performed from the outside such as an input operation performed by a user.

The control device 17 captures an image signal output from the receiving device 15 and applies predetermined image processing to the captured image signal to generate an in-vivo image. Further, the control device 17 captures a position detection signal output from the signal processing device 13 to calculates the position of the capsule endoscope 10 inside the subject 2 and allows the display device 18 to display the in-vivo image and the position of the capsule endoscope 10 in a predetermined form. Further, the control device 17 outputs a control signal to the signal generation device 14 in accordance with a signal input from the operation input device 16 to allow the magnetic field generation device 12 to generate a magnetic field for guiding the capsule endoscope 10. The control device 17 includes, for example, a work station and a personal computer.

Figure 3:
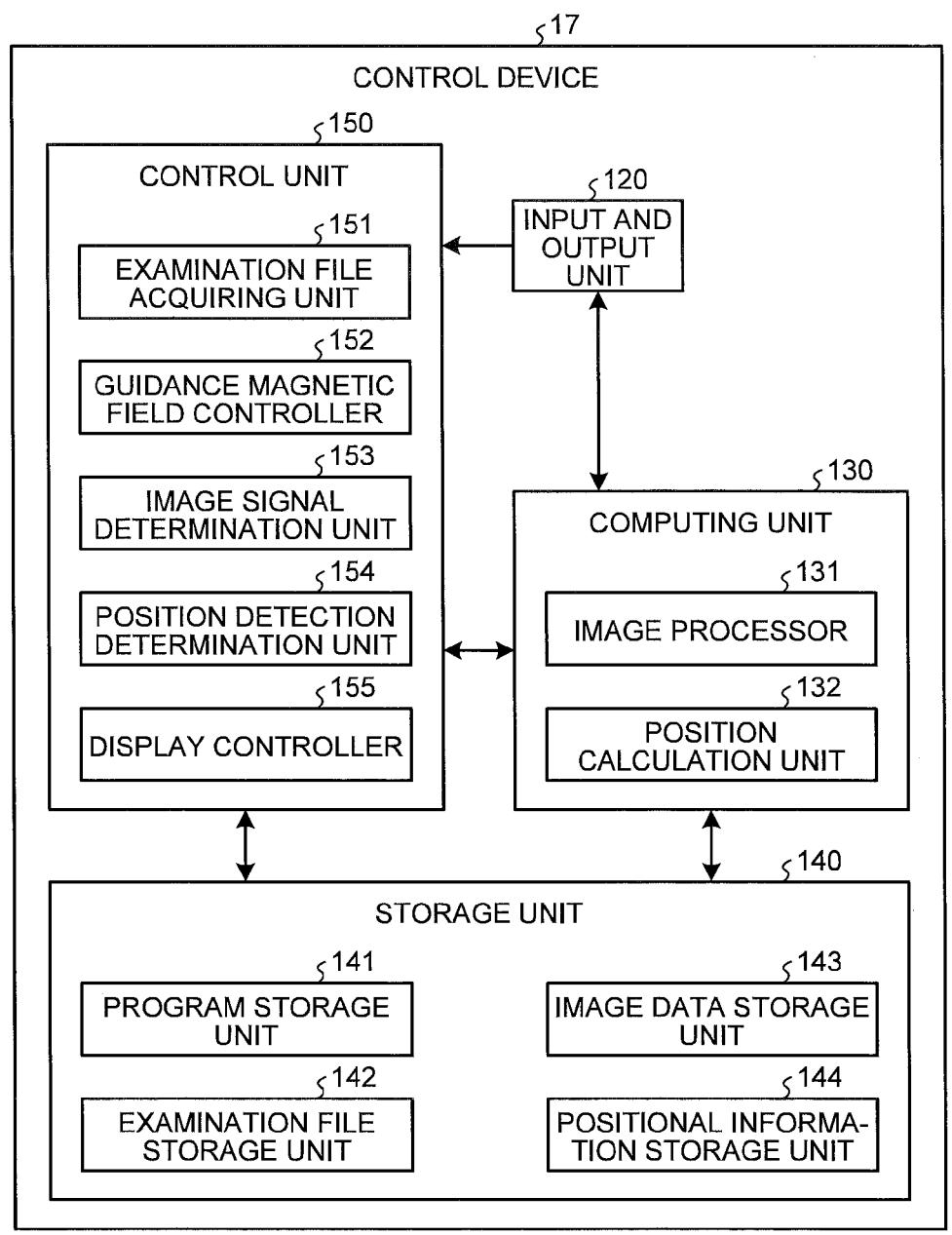
FIG. 3 is a block diagram illustrating an example of the configuration of a control device illustrated in FIG. 1.

FIG. 3 is a block diagram illustrating an example of the configuration of the control device 17. As illustrated in FIG. 3, the control device 17 is provided with an input and output unit 120, a computing unit 130, a storage unit 140, and a control unit 150.

The input and output unit 120 is an external interface which performs input and output of information with an external device. The input and output unit 120 receives various pieces of data and instruction signals output from external devices including the signal processing device 13, the receiving device 15, and the operation input device 16 and outputs the received data and instruction signals to the computing unit 130 or the control unit 150, and outputs various pieces of data and control signals output from the computing unit 130 or the control unit 150 to externals devices including the signal generation device 14 and the display device 18.

The computing unit 130 is implemented by hardware such as a CPU. The computing unit 130 reads various programs stored in a program storage unit 141 (described below) to apply predetermined calculation processing to various pieces of data input to the control device 17. More specifically, the computing unit 130 is provided with an image processor 131 and a position calculation unit 132.

The image processor 131 applies image processing such as white balance processing, demosaicing, color conversion, density conversion (gamma conversion), smoothing (noise removal), and sharpening (edge enhancement) to an image signal captured from the receiving device 15 to generate image data for display.

The position calculation unit 132 calculates the position of the capsule endoscope 10 inside the subject 2 in accordance with a position detection signal captured from the signal processing device 13 and generates positional information that indicates the position of the capsule endoscope 10.

The storage unit 140 is implemented by, for example, a semiconductor memory such as a flash memory, a RAM, and a ROM, a recording medium such as a HDD, a MO, a CD-R, and a DVD-R, and a writing and reading device. The storage unit 140 is provided with a program storage unit 141 which stores programs for operating the control device 17 to execute various functions and various pieces of information, an examination file storage unit 142 which stores an examination file, the examination file storing information about an examination to the subject 2, an image data storage unit 143 which stores image data for display generated by the image processor 131, and a positional information storage unit 144 which stores positional information generated by the position calculation unit 132.

The control unit 150 is implemented by hardware such as a CPU. The control unit 150 reads various programs stored in the program storage unit 141 to perform instruction or data transfer to the units constituting the control device 17 in accordance with various signals input to the control device 17 to totally control the operation of the entire control device 17.

More specifically, the control unit 150 is provided with an examination file acquiring unit 151 which acquires an examination file, a guidance magnetic field controller 152 which controls the signal generation device 14 on the basis of guidance instruction information input from the operation input device 16, an image signal determination unit 153 which determines whether normal image display is possible based on an image signal received by the receiving device 15, a position detection determination unit 154 which determines whether normal position detection for the capsule endoscope 10 is possible based on a position detection signal output from the signal processing device 13, and a display controller 155 which controls a display operation in the display device 18.

The examination file acquiring unit 151 acquires an examination file regarding the subject 2 to be examined in an examination using the capsule endoscope 10. Patient information such as a patient name, a patient ID, and the date of birth, information regarding examination contents such as an examination target site, and information such as an examination technician (doctor), an examination facility, and an ID of the used capsule endoscope 10 are recorded in the examination file and associated with an image signal acquired by the examination.

The examination file acquiring unit 151 may create an examination file in each examination on the basis of a signal that is input from the operation input device 16 in response to an input operation of a user or may acquire an examination file regarding the subject 2 to be examined from examination files previously created and stored in the examination file storage unit 142 when the examination is performed.

The guidance magnetic field controller 152 calculates a guidance direction and a guidance amount for the capsule endoscope 10 corresponding to an operation to the operation input device 16 on the basis of guidance instruction information input from the operation input device 16 and outputs a control signal corresponding to the guidance direction and the guidance amount to the signal generation device 14 to allow the signal generation device 14 to generate a signal for driving the magnetic field generation device 12.

The image signal determination unit (first determination unit) 153 determines whether normal image display is possible based on an image signal received by the receiving device 15 in accordance with a predetermined condition. Specifically, the image signal determination unit 153 determines that normal image display is possible when a vertical synchronization signal is detected from a received image signal. Alternatively, the image signal determination unit 153 may determine that the normal image display is possible when the received signal strength of the image signal is equal to or more than a predetermined value.

The position detection determination unit (second determination unit) 154 determines whether position detection for the capsule endoscope 10 is possible in accordance with a predetermined condition. For example, when the magnetic field generation unit 106 of the capsule endoscope 10 generates no alternating magnetic field or generates an alternating magnetic field having a low strength, the position detection device 11 cannot detect an alternating magnetic field having a sufficient strength. In this case, the signal processing device 13 outputs no position detection signal or outputs a position detection signal having a low strength. Thus, the position detection determination unit 154 determines that the normal position detection for the capsule endoscope 10 is possible when a position detection signal having a strength equal to or more than a predetermined threshold is captured from the signal processing device 13.

The display controller 155 allows the display device 18 to display an in-vivo image based on image data to which image processing has been applied by the image processor 131 and related information such as patient information, positional information, and body posture information in a predetermined form in real time during examination using the capsule endoscope 10.

The display device 18 is a display unit capable of displaying an in-vivo image and related information thereof. The display device 18 is configured using a liquid crystal display or an organic electro luminescence (EL) display.

Figure 4:
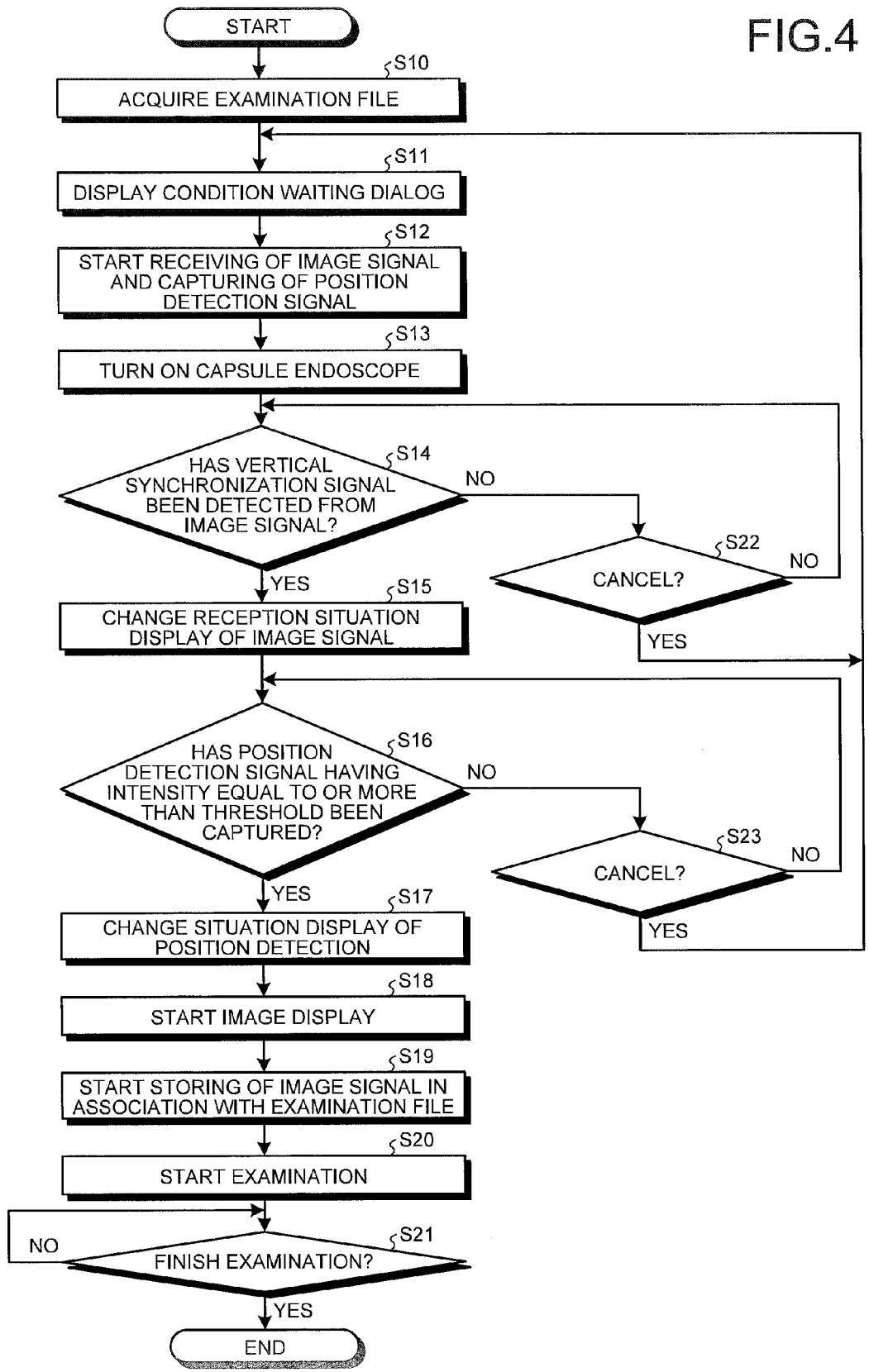
FIG. 4 is a flow chart illustrating the operation of the capsule endoscope system illustrated in FIG. 1.
Figure 5:
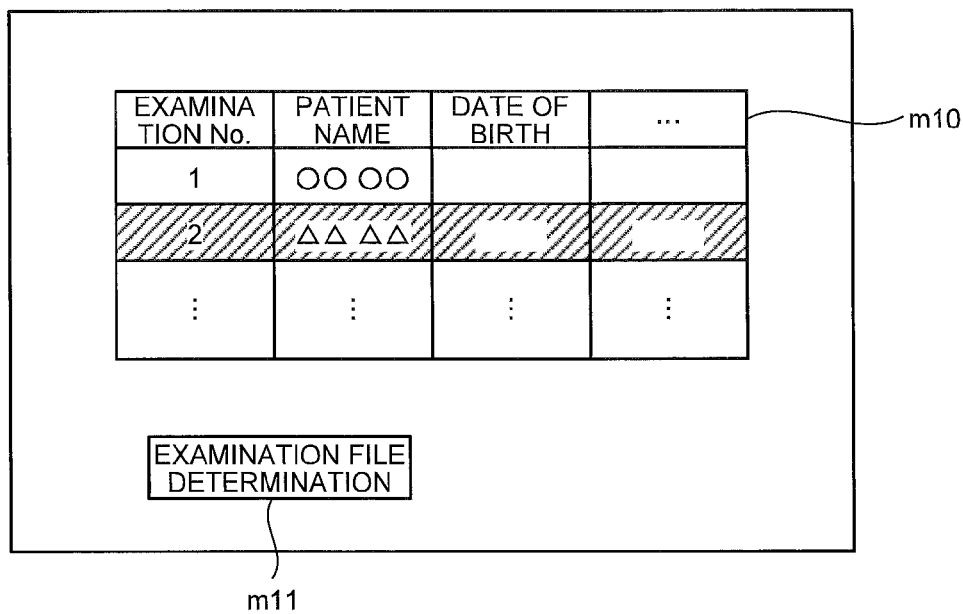
FIG. 5 is a schematic diagram illustrating an example of an examination selection screen displayed on a display device illustrated in FIG. 1.

Next, the operation of the capsule endoscope system 1 will be described. FIG. 4 is a flow chart illustrating the operation of the capsule endoscope system 1. First, in step S10, the control unit 150 acquires an examination file regarding a subject 2 to be examined. More specifically, as illustrated in FIG. 5, the display controller 155 allows the display device 18 to display an examination selection screen M1 which includes an examination file list m10 stored in the examination file storage unit 142. When one file is selected by a predetermined pointer operation (for example, a click) using the operation input device 16 (for example, a touch panel or a mouse) on the examination selection screen M1 and an examination file determination button m11 is depressed, the examination file acquiring unit 151 reads the selected examination file from the examination file storage unit 142. FIG. 5 indicates that an examination file of an examination number (No.) 2 has been selected. Alternatively, the examination file acquiring unit 151 may create a new examination file in accordance with a signal that is output from the operation input device 16 in response to an input operation of a user.

Figure 6:
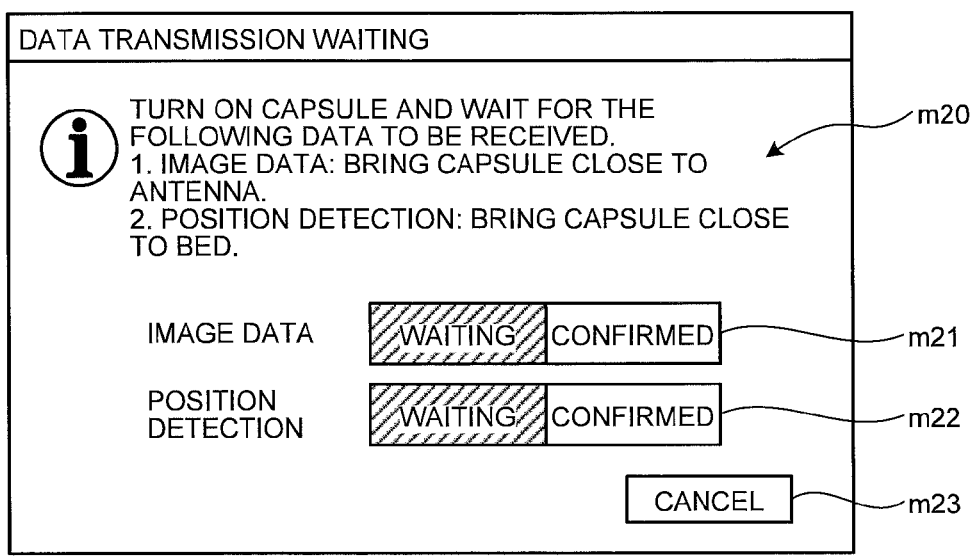
FIG. 6 is a schematic diagram illustrating a condition waiting dialog displayed on the display device illustrated in FIG. 1.

In step S11, the display controller 155 allows the display device 18 to display a condition waiting dialog M2 illustrated in FIG. 6. The condition waiting dialog M2 is a screen that represents whether two conditions, specifically, a condition that the normal image display is possible based on the image signal transmitted from the capsule endoscope 10 and a condition that the normal position detection for the capsule endoscope 10 is possible, have been satisfied. The condition waiting dialog M2 includes a text message m20 such as "TURN ON CAPSULE AND WAIT FOR THE FOLLOWING DATA TO BE RECEIVED", a reception situation display field m21 which indicates a reception situation of an image signal, a position detection situation display field m22 which indicates a position detection situation for the capsule endoscope 10, and a cancel button m23. The reception situation display field m21 includes display of "WAITING" and "CONFIRMED". The position detection situation display field m22 includes display of "WAITING" and "CONFIRMED". In both the reception situation display field m21 and the position detection situation display field m22, "WAITING" is active when the condition waiting dialog M2 is first displayed.

In step S12, the receiving device 15 starts an operation of receiving an image signal from the capsule endoscope 10, and the signal processing device 13 starts an operation of capturing a detection signal of an alternating magnetic field from the position detection device 11. At this time, even when an image signal is input from the receiving device 15, the control unit 150 perform control for inhibiting display of an image based on the image signal by the display device 18 and inhibiting storage of the image signal into the storage unit 140 in the control device 17.

When a user turns on the capsule endoscope 10 in accordance with the text message m20 in step S13, the capsule endoscope 10 starts imaging, transmission of an image signal, and generation of an alternating magnetic field. Accordingly, when the capsule endoscope 10 normally operates, an image signal is received by the receiving device 15 and captured by the control device 17, and the image processor 131 starts image processing. In addition, a detection signal of an alternating magnetic field detected by the position detection device 11 is captured by the signal processing device 13, and the position calculation unit 132 starts calculation of the position of the capsule endoscope 10 on the basis of the position detection signal output from the signal processing device 13.

In step S14, the image signal determination unit 153 determines whether an image signal has been captured from the receiving device 15 and a vertical synchronization signal has been detected from the captured image signal.

Figure 7:
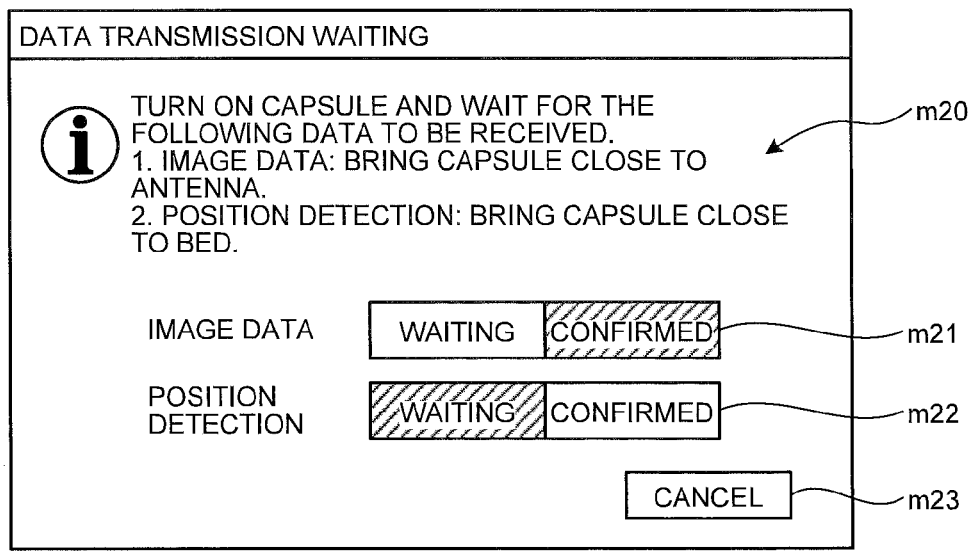
FIG. 7 is a schematic diagram illustrating the condition waiting dialog displayed on the display device illustrated in FIG. 1.

When the vertical synchronization signal has been detected from the image signal (Yes in step S14), the image signal determination unit 153 determines that the normal image display based on the image signal is possible, and the display controller 155 performs control for changing the reception situation display of the image signal in the condition waiting dialog M2 (step S15). Accordingly, as illustrated in FIG. 7, the display of "WAITING" in the reception situation display field m21 becomes inactive, and the display of "CONFIRMED" becomes active.

In the following step S16, the position detection determination unit 154 determines whether a position detection signal has been captured from the signal processing device 13 and the strength of the signal detection signal is equal to or more than a predetermined threshold.

Figure 8:
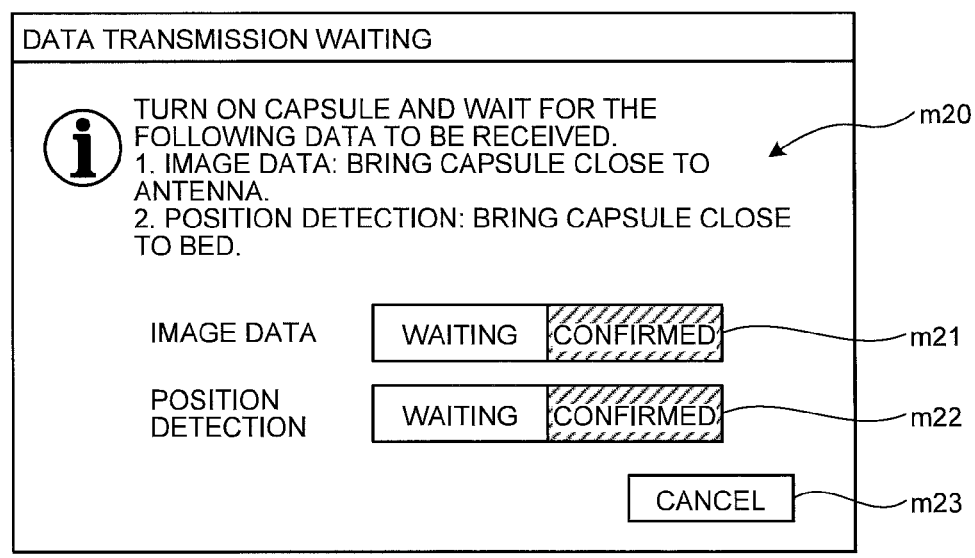
FIG. 8 is a schematic diagram illustrating the condition waiting dialog displayed on the display device illustrated in FIG. 1.

When a position detection signal having a strength equal to or more than the threshold (Yes in step S16), the position detection determination unit 154 determines that the normal position detection for the capsule endoscope 10 is possible, and the display controller 155 performs control for changing the situation display of the position detection in the condition waiting dialog M2 (step S17). Accordingly, as illustrated in FIG. 8, the display of "WAITING" in the position detection situation display field m22 becomes inactive, and the display of "CONFIRMED" becomes active.

The determination in step S14 and the determination in step S16 may be simultaneously performed in parallel. In this case, the display change in step S15 and the display change in step S17 are performed in any order as needed when detection of a vertical synchronization signal or capturing of a position detection signal having a strength equal to or more than the threshold is confirmed.

In step S18, the control unit 150 releases the inhibition of image display based on an image signal captured from the receiving device 15 and allows the display device 18 to start image display. Accordingly, the display device 18 sequentially displays the images of the object captured by the capsule endoscope 10.

In step S19, the control unit 150 releases the inhibition of storage of an image signal captured from the receiving device 15 and allows the image data storage unit 143 to start storage of an image signal. Accordingly, the image data storage unit 143 sequentially stores image signals which are captured from the receiving device 15 and then image-processed by the image processor 131 in association with the examination file. In this case, a unique ID of the capsule endoscope 10 whose normal operation has been confirmed is registered in the examination file.

Upon confirming that both the display of "CONFIRMED" in the reception situation display field m21 and the display of "CONFIRMED" in the position detection situation display field m22 are active in the condition waiting dialog M2, a user allows the subject 2 to swallow the capsule endoscope 10. Accordingly, an examination is started (step S20), and an image inside the subject 2 captured by the capsule endoscope 10 is displayed on the display device 18.

In step S21, the control unit 150 determines whether to finish the examination using the capsule endoscope 10. For example, when an input operation for finishing the examination has been performed by a user or when output of an image signal from the receiving device 15 has been stopped (that is, wireless transmission of an image signal from the capsule endoscope 10 has been stopped), the control unit 150 determines to finish the examination. When the control unit 150 has determined not to finish the examination (No in step S21), the capsule endoscope system 1 continues the examination. When the control unit 150 has determined to finish the examination (Yes in step S21), the operation of the capsule endoscope system 1 is finished.

In step S14, when no vertical synchronization signal has been detected from the image signal (No in step S14), the control unit 150 determines whether an instruction signal for cancelling the determination operation has been input (step S22). The cancel instruction signal is input when a predetermined pointer operation using the operation input device 16 is performed with respect to the cancel button m23 in the condition waiting dialog M2. When no cancel instruction signal has been input (No in step S22), the operation of the control unit 150 returns to step S14. On the other hand, when the cancel instruction signal has been input (Yes in step S22), the operation of the capsule endoscope 10 proceeds to step S11. In this case, a user discards the capsule endoscope 10 after turning off the power thereof, and prepares another capsule endoscope 10.

In step S16, when no position detection signal having a strength equal to or more than the threshold has been captured (No in step S16), the control unit 150 determines whether an instruction signal for cancelling the determination operation has been input (step S23). The cancel instruction signal is input when a predetermined pointer operation using the operation input device 16 is performed with respect to the cancel button m23 in the condition waiting dialog M2. When no cancel instruction signal has been input (No in step S23), the operation of the control unit 150 returns to step S16. On the other hand, when the cancel instruction signal has been input (Yes in step S23), the operation of the capsule endoscope 10 proceeds to step S11. In this case, a user discards the capsule endoscope 10 after turning off the power thereof, and prepares another capsule endoscope 10.

As described above, in the embodiment, until both the practicability of normal image display based on an image signal received from the capsule endoscope 10 and the practicability of the normal position detection for the capsule endoscope 10 are confirmed, the display device 18 is not allowed to display an image based on the received image signal and the storage unit 140 is not allowed to store the image signal. Thus, even when there is a failure of a generation or transmission operation of an image signal or a failure of a magnetic field generation operation for position detection in a prepared capsule endoscope 10, it is possible to prevent an image signal transmitted from the capsule endoscope 10 from being processed as examination information. Thus, it is possible to reduce accumulation of unnecessary information that is not used in diagnosis by a doctor to simplify information management. Further, even when a prepared capsule endoscope 10 is replaced with another capsule endoscope due to a failure, an examination file once acquired can be used as it is. This eliminates the necessity of issuing a new examination file. Thus, a load on a user can be reduced.

First Modification

Next, a capsule endoscope system according to a first modification of the embodiment of the present invention will be described. In the above embodiment, when no vertical synchronization signal has been detected from an image signal (No in step S14) or no position detection signal having a strength equal to or more than the threshold has been captured (No in step S16), the determination operation is cancelled by determination of a user. However, when a vertical synchronization signal has been detected from an image signal, but no position detection signal having a strength equal to or more than the threshold has been captured for a predetermined time, or when a position detection signal having a strength equal to or more than the threshold has been captured, but no vertical synchronization signal has been detected from an image signal for a predetermined time, the control unit 150 may automatically cancel the determination operation.

Figure 9:
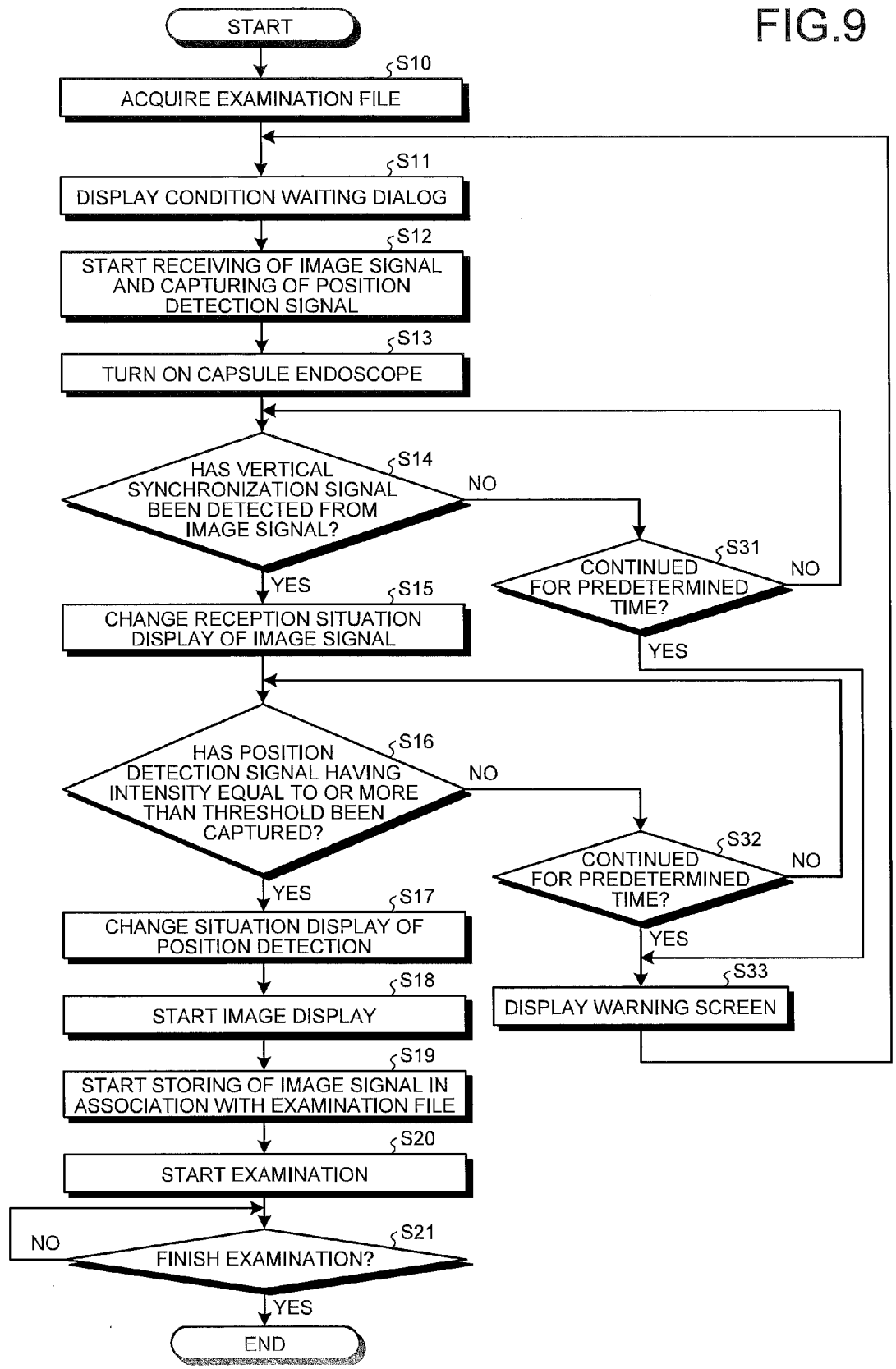
FIG. 9 is a flow chart illustrating the operation of a capsule endoscope system according to a first modification of the embodiment of the present invention.

FIG. 9 is a flow chart illustrating the operation of the capsule endoscope system according to the first modification. Steps S10 to S21 of FIG. 9 are the same as those of the above embodiment.

When no vertical synchronization signal has been detected in step S14 (No in step S14), the image signal determination unit 153 determines whether a state in which no vertical synchronization signal is detected has continued for a predetermined time (step S31). When the state has continued for the predetermined time (Yes in step S31), the image signal determination unit 153 stops the determination operation for determining whether a vertical synchronization signal has been detected from an image signal, and the operation of the capsule endoscope system 1 proceeds to step S33. On the other hand, when the state has not yet continued for the predetermined time (No in step S31), the image signal determination unit 153 continues the determination operation for determining whether a vertical synchronization signal has been detected from an image signal (step S14).

When no position detection signal having a strength equal to or more than the threshold has been captured in step S16 (No in step S16), the position detection determination unit 154 determines whether a state in which a position detection signal having a strength equal to or more than the threshold is not captured has continued for a predetermined time (step S32). When the state has continued for the predetermined time (Yes in step S32), the position detection determination unit 154 stops the determination operation for determining whether a position detection signal having a strength equal to or more than the threshold has been captured, and the operation of the capsule endoscope system 1 proceeds to step S33. On the other hand, when the state has not yet continued for the predetermined time (No in step S32), the position detection determination unit 154 continues the determination operation for determining whether a position detection signal having a strength equal to or more than the threshold has been captured (step S16).

Figure 10:
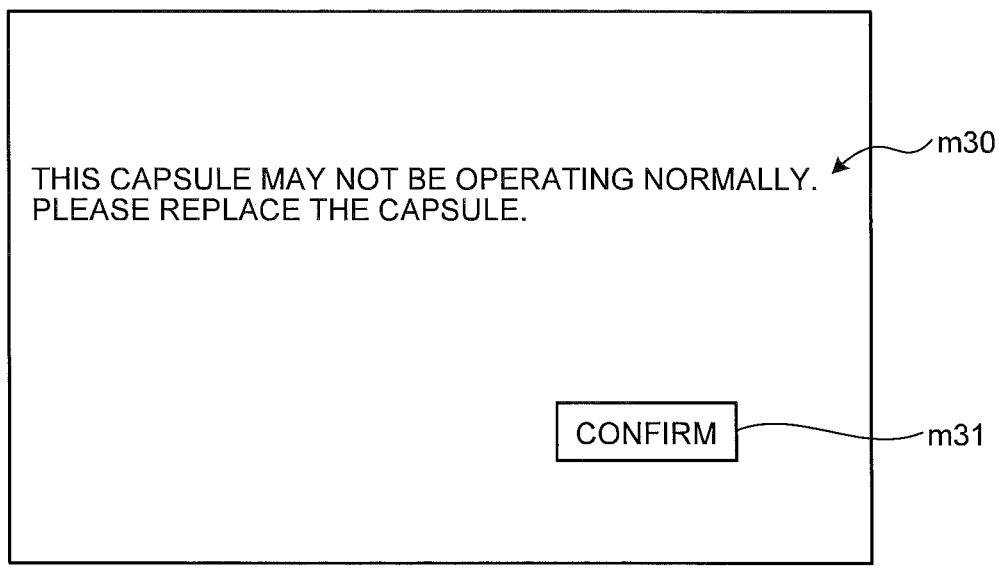
FIG. 10 is a schematic diagram illustrating a warning screen displayed in the first modification of the embodiment of the present invention.

In step S33, the display controller 155 allows the display device 18 to display a warning screen for warning a failure in the capsule endoscope 10. FIG. 10 is a schematic diagram illustrating an example of the warning screen. A warning screen M3 illustrated in FIG. 10 includes a text massage m30 which urges a user to replace the capsule endoscope 10 such as "THIS CAPSULE MAY NOT BE OPERATING NORMALLY. PLEASE REPLACE THE CAPSULE." and a confirmation button m31.

When such a warning screen M3 is displayed, a user discards the capsule endoscope 10 after turning off the power thereof, and prepares another capsule endoscope 10. When a pointer operation using the operation input device 16 with respect to the confirmation button m31 is performed, the operation of the capsule endoscope system 1 returns to step S11.

Second Modification

A position detection method applicable to the capsule endoscope system 1 is not limited to the above method based on an alternating magnetic field, and various known methods may be applied. For example, the position of the capsule endoscope 10 inside the subject 2 may be estimated based on a received signal strength distribution of an image signal received by each of the antennas 15a. In this case, the magnetic field generation unit 106 is not required in the capsule endoscope 10.

In this case, the position calculation unit 132 captures the strength of an image signal received by each of the antennas 15a from the receiving device 15 and performs calculation for estimating the position of the capsule endoscope 10 from these image signal strengths and the arrangement positions of the antennas 15a.

Further, in this case, the position detection determination unit 154 determines that position detection for the capsule endoscope 10 is possible when the strength of the image signal received by each of the antennas 15a is equal to or more than a predetermined threshold. In this determination, the position detection determination unit 154 may determine that the position detection is possible when all antennas have a strength equal to or more than the threshold or when at least one antenna has a strength equal to or more than the threshold.

According to some embodiments, when it is determined that normal image display based on an image signal received from the capsule endoscope is possible and normal position detection for the capsule endoscope is possible, the image display unit is allowed to start display of an image based on the image signal. That is, an image based on the image signal is not displayed on the image display unit until both normal image display and normal position detection are determined to be possible. Thus, when a capsule endoscope has a failure, it is possible to prevent an image signal transmitted from the capsule endoscope from being processed as examination information.

The above-described embodiments and modifications of the present invention are merely examples for embodying the present invention, and the present invention is not limited to the above-described embodiments and modifications. The present invention may form various inventions by appropriately combining a plurality of elements disclosed in the embodiments and the first modification. The present invention can be modified in various manners in accordance with specifications. Further, it is obvious from the above description that other various embodiments are implemented within the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope system comprising:
    a capsule endoscope comprising:
        an image sensor configured to image an object to generate an image signal; and
        a wireless transmitter configured to wirelessly transmit the image signal generated by the image sensor;
    a receiver configured to receive the image signal transmitted from the capsule endoscope; and
    a processor comprising hardware, wherein the processor is configured to:
        output a position detection signal of the capsule endoscope;
        determine whether a vertical synchronization signal has been detected from the image signal or a received signal strength of the image signal received by the receiver is equal to or more than a first threshold;
        determine whether the position detection signal has a strength equal to or more than a second threshold; and
        control a display to start display of the image based on the image signal;
        (i) when the vertical synchronization signal has been detected from the image signal and the position detection signal has a strength equal to or more than the second threshold; or
        (ii) when the received signal strength of the image signal is equal to or more than the first threshold and the position detection signal has a strength equal to or more than the second threshold.

2. The capsule endoscope system according to claim 1, further comprising a first memory configured to store the image signal,
    wherein: (i) when the vertical synchronization signal has been detected from the image signal and the position detection signal has a strength equal to or more than the second threshold, or (ii) when the received signal strength of the image signal is equal to or more than the first threshold and the position detection signal has a strength equal to or more than the second threshold, the processor is further configured to cause the first memory to start storage of the image signal.

3. The capsule endoscope system according to claim 2, further comprising:
    a second memory configured to store information on a subject into which the capsule endoscope is configured to be introduced,
    wherein the processor is configured to acquire an examination file based on the information on the subject, and
    wherein (i) when the vertical synchronization signal has been detected from the image signal and the position detection signal has a strength equal to or more than the second threshold, or (ii) when the received signal strength of the image signal is equal to or more than the first threshold and the position detection signal has a strength equal to or more than the second threshold, the processor is configured to cause the first memory to store the image signal such that the image signal associates with the examination file.

4. The capsule endoscope system according to claim 1,
    wherein the processor is configured to cause the display to display a dialog for instructing a user to wait until (iii) the vertical synchronization signal has been detected from the image signal and the position detection signal has a strength equal to or more than the second threshold, or until (iv) the received signal strength of the image signal is equal to or more than the first threshold and the position detection signal has a strength equal to or more than the second threshold.

5. The capsule endoscope system according to claim 4,
    wherein the dialog includes a display field for displaying results of determination made by the processor while continually updating the results.

6. The capsule endoscope system according to claim 1,
    wherein the capsule endoscope comprises a magnetic field generator configured to generate an alternating magnetic field, and
    wherein the processor is configured to output the position detection signal when the alternating magnetic field is detected.

7. A capsule endoscope system comprising:
    a capsule endoscope comprising:
        an image sensor configured to image an object to generate an image signal; and
        a wireless transmitter configured to wirelessly transmit the image signal generated by the image sensor;
    a receiver comprising a plurality of antennas, each of which is configured to receive the image signal transmitted from the capsule endoscope; and a processor comprising hardware, wherein the processor is configured to:
  detect a position of the capsule endoscope based on a received signal strength distribution of the image signal received by each of the plurality of antennas;
  determine whether a vertical synchronization signal has been detected from the image signal or a received signal strength of the image signal received by the receiver is equal to or more than a first threshold;
  determine whether at least one of received signal strengths of the image signal received by the plurality of antennas is equal to or more than a second threshold; and
  control a display to start display of the image based on the image signal:
    (i) when the vertical synchronization signal has been detected from the image signal and at least one of the received signal strengths of the image signal is equal to or more than the second threshold; or
    (ii) when the received signal strength of the image signal is equal to or more than the first threshold and at least one of the received signal strengths of the image signal is equal to or more than the second threshold.

* * * * *